US006500818B1

(12) United States Patent
Bernstein et al.

(10) Patent No.: US 6,500,818 B1
(45) Date of Patent: Dec. 31, 2002

(54) NAPHTHALENECARBOXAMIDES AS TACHYKININ RECEPTOR ANTAGONISTS

(75) Inventors: Peter Robert Bernstein, Wilmington, DE (US); Robert Frank Dedinas, Wilmington, DE (US); Cyrus John Ohnmacht, Wilmington, DE (US); Keith Russell, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/806,620

(22) PCT Filed: Oct. 4, 1999

(86) PCT No.: PCT/GB99/03273

§ 371 (c)(1),
(2), (4) Date: Mar. 30, 2001

(87) PCT Pub. No.: WO00/20003

PCT Pub. Date: Apr. 13, 2000

(30) Foreign Application Priority Data

Oct. 7, 1998 (GB) ................................................ 9821703
Mar. 9, 1999 (GB) ................................................ 9905238

(51) Int. Cl.$^7$ .................... C07D 401/04; C07D 417/04; A61K 31/454; A61K 31/4545; A61P 25/24
(52) U.S. Cl. .................. 514/211.01; 546/187; 546/188; 546/205; 546/206; 546/197; 544/3; 544/8; 544/332; 540/492; 540/524; 540/544; 540/545; 514/211.08; 514/212.08; 514/218; 514/316; 514/319; 514/321; 514/222.5; 514/222.2; 514/274
(58) Field of Search ................................ 546/188, 187, 546/205, 206, 197; 544/332, 8, 3; 540/492, 545, 544, 524; 514/211.01, 211.08, 212.08, 218, 316, 319, 321, 222.5, 222.2, 274

(56) References Cited

FOREIGN PATENT DOCUMENTS

| EP | 0 428 434 A | 5/1991 |
|---|---|---|
| EP | 0 474 561 A | 3/1992 |
| EP | 0 515 240 A | 11/1992 |
| EP | 0 559 538 A | 9/1993 |
| EP | 0 630 887 A | 12/1994 |

OTHER PUBLICATIONS

Emonds–Alt X Et Al: "Pharmacological Profile and Chemical Synthesis of SR 48968, A Non–Peptide Antagonist of the Neurokinin A (NK2) Receptor" Bioorganic & Medicinal Chemistry Letters, vol. 3, No. 5, Jan. 1, 1993, pp. 925–930, XP002068450.

*Primary Examiner*—Mark L. Berch
*Assistant Examiner*—Kahsay Habte
(74) *Attorney, Agent, or Firm*—Kenneth F. Mitchell

(57) ABSTRACT

Compounds having the following formula

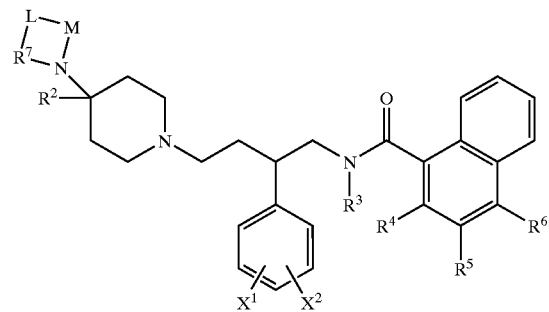

wherein L, M, $R^2$, $R^3$, $R^4$, $R^5$, $R^6$, $R^7$, $X^1$ and $X^2$ are as defined in the specification, pharmaceutically-acceptable salt thereof, useful for treating depression, anxiety, asthma, rheumatoid arthritis, Alzheimer's disease, cancer, schizophrenia, oedema, allergic rhinitis, inflammation, pain, gastrointestinal-hypermotility, emesis, Huntington's disease, psychoses, hypertension, migraine, bladder hypermotility, or urticaria, compositions including such compounds and processes for making such compounds.

13 Claims, No Drawings

NAPHTHALENECARBOXAMIDES AS TACHYKININ RECEPTOR ANTAGONISTS

BACKGROUND

The mammalian neurokinins comprise a class of peptide neurotransmitters which are found in the peripheral and central nervous systems. The three principal neurokinins are Substance P (SP), Neurokinin A (NKA) and Neurokinin B (NKB).

There are also N-terminally extended forms of at least NKA. At least three receptor types are known for the three principal neurokinins. Based upon their relative selectivities favoring the neurokinin agonists SP, NKA and NKB, the receptors are classified as neurokinin 1 ($NK_1$), neurokinin 2 ($NK_2$) and neurokinin 3 ($NK_3$) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation, increased mucus secretion and activation of mast cells. Thus, the tachykinins are implicated in the pathophysiology and airway hyperresponsiveness observed in asthmatics; and blockade of the action of released tachykinins may be useful in the treatment of asthma and related conditions. A cyclopeptide antagonist (FK-224) selective for both $NK_1$ and $NK_2$ receptors has demonstrated clinical efficacy in human patients suffering from asthma and chronic bronchitis. M. Ichinose, et al., *Lancet,* 1992, 340, 1248.

DESCRIPTION

This invention relates to naphthalenecarboxamide compounds N-substituted by an substituted piperidinylbutyl group, to pharmaceutical compositions containing such compounds, as well as to their uses and processes for their preparation. These compounds antagonize the pharmacological actions of the endogenous neuropeptide tachykinins known as neurokinins, particularly at the neurokinin 1 ($NK_1$) and the neurokinin 2 ($NK_2$) receptors. These compounds are useful whenever such antagonism is desired. Thus, such compounds are of value in the treatment of those diseases in which Substance P and Neurokinin A are implicated, for example, in the treatment of asthma, anxiety, depression, emesis, urinary incontinence and related conditions.

The N-substituted naphthalenecarboxamide compounds of the present invention show a high degree of both $NK_1$ and/or $NK_2$ receptor antagonist activity. Additionally, by manipulation of the substituents on the naphthalene and piperidine rings of the formula (I), the ratio of activity at the $NK_1$ and $NK_2$ receptors can be modified as desired, affording compounds that are predominantly active at either $NK_1$ or $NK_2$ receptors, or affording compounds with a balanced activity and, as such, are particularly useful when combined antagonism of both receptors is desired. In particular, the compounds of the present invention also possess a high degree of $NK_1$ and/or $NK_2$ antagonism upon oral administration.

Accordingly, the present invention provides the compounds of the general formula (I):

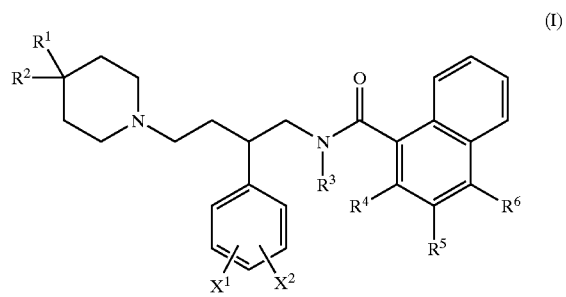

wherein:
$R^1$, in one respect, has the formula

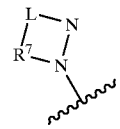

wherein $R^7$ is as defined below to give general formula (Ia).

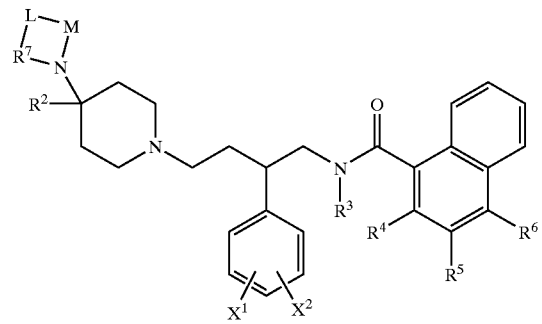

$R^2$ is hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl or di-$C_{1-6}$alkylcarbamoyl.

$R^3$ is hydrogen or $C_{1-6}$alkyl for example methyl, ethyl, n-propyl or cyclopropyl. Preferably, $R^3$ is methyl.

$R^4$, $R^5$ and $R^6$ are each, independently, hydroxy; cyano; nitro; trifluoromethoxy; trifluoromethyl; $C_{1-6}$alkylsulfonyl for example methylsulphonyl; halo for example chloro, bromo, fluoro or iodo; $C_{1-6}$alkoxy for example methoxy, ethoxy or propoxy; $C_{1-6}$alkyl for example methyl or ethyl; cyano$C_{1-6}$alkyl for example cyanomethyl; $C_{2-6}$alkenyl for example ethenyl, prop-1-enyl or prop-2-enyl; $C_{2-6}$alkynyl for example ethynyl; carboxy, $C_{1-6}$alkoxycarbonyl for example methoxycarbonyl; carbamoyl; $C_{1-6}$alkylcarbamoyl for example methylcarbamoyl or ethylcarbamoyl; di-$C_{1-6}$alkylcarbamoyl for example di-methylcarbamoyl; $C_{1-6}$alkanoyl for example acetyl or propionyl; $C_{1-6}$alkanoylamino for example acetylamino or propionylamino; aminosulfonyl; and substituted $C_{1-6}$alkyl for example methyl substituted by any of the hereinabove substituents. Additionally, $R^6$ may be hydrogen.

Favourably, $R^4$ is $C_{1-6}$alkyl for example methyl or ethyl; $C_{1-6}$alkoxy for example methoxy or ethoxy; or halo for example fluoro, chloro, bromo or iodo. Preferably, $R^4$ is methyl, ethyl, methoxy, ethoxy or fluoro. More preferably, $R^4$ is methoxy or ethyl, most preferably, methoxy.

Preferably, $R^5$ is cyano or nitro; more preferably, $R^5$ is cyano.

Preferably, $R^6$ is hydrogen, methoxy, cyano or nitro.

$R^7$ is —$CH_2CH_2$—, —$CH_2CH_2CH_2$— or —$CH_2CH_2CH_2CH_2$—.

M is —C(=O)— or —S(=O)$_2$—.

L is NH or $CH_2$.

The compounds of the present invention possess a number of chiral centres, at —CH(Ph-$X^1$,$X^2$)—, and possibly in the optional substituents (for example the MeSO— substituent) on either (or both) of the phenyl and naphth-1-yl groups. The present invention covers all isomers, diastereoisomers and mixtures thereof that antagonise $NK_1$ and/or $NK_2$.

The preferred configuration at —CH(Ph-$X^1$,$X^2$)— is shown in formula (Ib) hereinbelow:

(Ib)

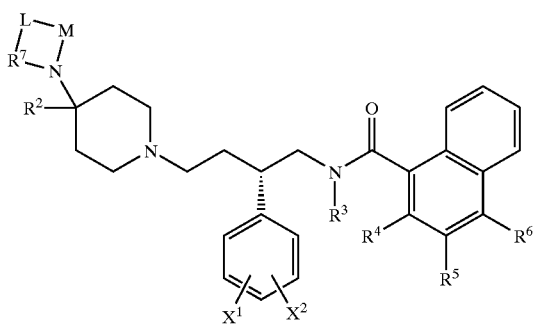

$X^1$ and $X^2$ are independently hydrogen or halo, provided that at least one of $X^1$ or $X^2$ is halo. Favourably, $X^1$ and $X^2$ are both chloro. In a preferred aspect Ph-$X^1$,$X^2$ is 3,4-dichlorophenyl.

$R^2$ is hydrogen; hydroxy; $C_{1-6}$alkoxy for example methoxy or ethoxy; $C_{1-6}$alkanoyloxy for example acetyloxy or propionyloxy; $C_{1-6}$alkanoyl for example acethyl or propionyl; $C_{1-6}$alkoxycarbonyl for example methoxycarbonyl or ethoxycarbonyl; $C_{1-6}$alkanoylamino for example acetylamino; $C_{1-6}$alkyl for example metrhyl or ethyl; carbamoyl; $C_{1-6}$alkylcarbamoyl for example methylcarbamoyl or ethylcarbamoyl or di-$C_{1-6}$ alkylcarbamoyl for example dimethylcarbamoyl.

Preferably, $R^2$ is hydrogen, hydroxy, methoxycarbonyl, methylcarbamoyl or dimethylcarbamoyl. More preferably $R^2$ is hydrogen or methylcarbamoyl.

A preferred class of compounds is that of the formula (II):

(II)

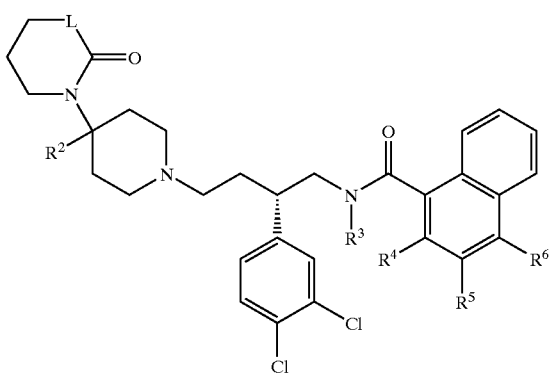

wherein $R^3$ is as hereinbefore defined and $R^4$—$R^6$ are selected from hydrogen, cyano, nitro, methoxy, methyl, ethyl and fluoro.

The most preferred structure is

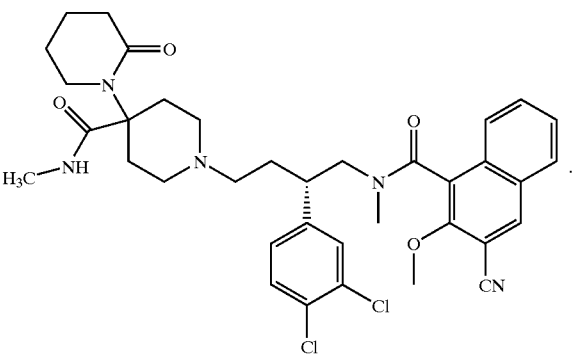

Particular compounds of this invention are provided as the Examples hereinbelow. $C_{Y-Z}$alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "$C_{4-7}$alkyl":

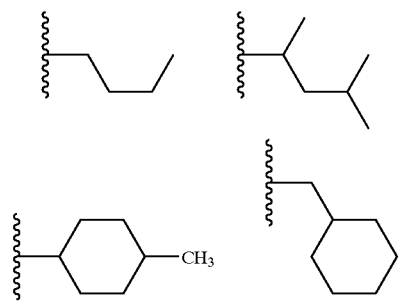

Pharmaceutically-acceptable salts may be prepared from the corresponding acid in conventional manner. Non-pharmaceutically-acceptable salts may be useful as intermediates and as such are another aspect of the present invention.

The compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl;

diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Therefore in a further aspect, the present invention provides a compound of the formula (I) or a pharmaceutically acceptable salt thereof for use in a method of therapeutic treatment of the human or animal body.

In yet a further aspect the present invention provides a method of treating a disease condition wherein antagonism of the $NK_1$ and/or $NK_2$ receptors is beneficial which comprises administering to a warm-blooded animal an effective amount of a compound of the formula (I) or a pharmaceutically-acceptable salt thereof The present invention also provides the use of a compound of the formula (I) or a pharmaceutically acceptable salt thereof in the preparation of a medicament for use in a disease condition wherein antagonism of the $NK_1$ and/or $NK_2$ receptors is beneficial.

The compounds of the formula (I) and their pharmaceutically acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

In another aspect the present invention provides a process for preparing a compound of the formula (I) or a pharmaceutically acceptable salt thereof which process comprises:

a) reacting a compound of the formula (III) with a compound of the formula (IV):

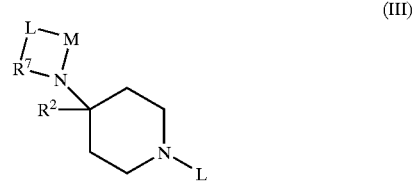

(III)

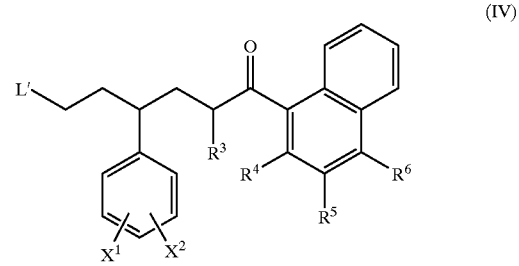

(IV)

wherein $R^2$—$R^7$, L, M, $X_1$ and $X_2$ are as hereinbefore defined; and L and L' are groups such that reductive amination of the formulae (III) and (IV) forms a N—C bond; or b) reacting a compound of the formula (V) with a compound of the formula (VI):

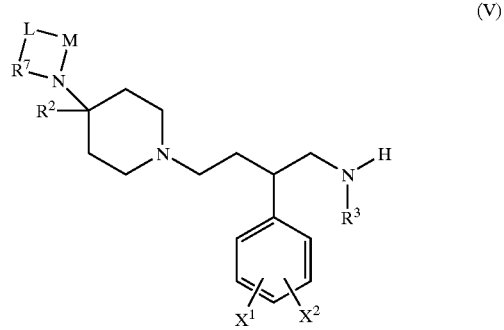

(V)

-continued (VI)

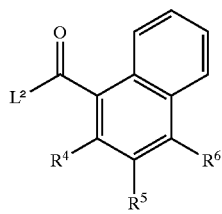

wherein R²—R⁷, L, M, X¹ and X₂ are as hereinbefore defined; and L" is a leaving group;

wherein any other functional group is protected, if necessary, and:
i) removing any protecting groups;
ii) optionally forming a pharmaceutically acceptable salt.

Protecting groups may in general be chosen from any of the groups described in the literature or known to the skilled chemist as appropriate for the protection of the group in question, and may be introduced and removed by conventional methods; see for example Protecting Groups in Organic Chemistry; Theodora W. Greene. Methods of removal are chosen so as to effect removal of the protecting group with minimum disturbance of groups elsewhere in the molecule.

It will also be appreciated that certain of the various optional substituents in the compounds of the formula (I) may be introduced by standard aromatic substitution reactions or generated by conventional functional group modifications either prior to or immediately following the processes described hereinabove. The reagents and reaction conditions for such procedures are well known in the chemical art.

The compounds of the formulae (III) and (IV) are reacted under conditions of reductive amination. Typically in the compounds of the formula (III) L is hydrogen.

Typically in the compounds of the formula (IV) L' is an oxo group so forming an aldehyde moiety. The reaction is typically performed at a non-extreme temperature, for example 0–100° C., suitably ambient temperature in a substantially inert solvent for example dichloromethane. Typical reducing agents include borohydrides such as sodium cyanoborohydride.

The compounds of the formula (III) are known or made be prepared in conventional manner. The compounds of the formula (IV) may be prepared, for example, by reacting a compound of the formula (VI) with a compound of the formula (VII):

(VII)

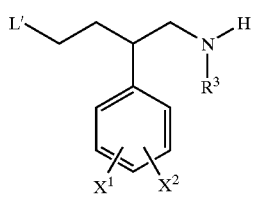

wherein L', R³, X¹ and X² are as hereinbefore defined under conventional acylation conditions.

The compounds of the formulae (V) and (VI) may be reacted under conventional acylation conditions wherein

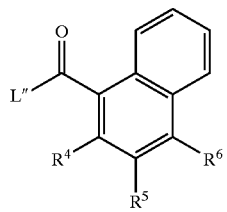

is an acid or an activated acid derivative. Such activated acid derivatives are well known in the literature. They may be formed in situ from the acid or they may be prepared, isolated and subsequently reacted. Typically L" is chloro thereby forming the acid chloride. Typically the acylation reaction is performed in the presence of a non-nucleophilic base, for example di-isopropylethylamine, in a substantially inert solvent at a non-extreme temperature.

The compounds of the formula (VII) are known or may be prepared in conventional manner. Certain compounds of the formulae (IV) and (VI) are novel and form part of the present invention. In particular the compounds of the formula (VI) wherein the naphth-1-yl group is substituted by a methoxy group at the 2-position and by a cyano group at the 3-position are novel.

Accordingly, in another aspect the present invention provides a compound of the formula (VIII):

(VIII)

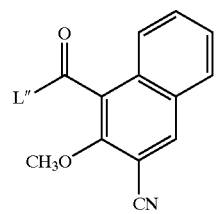

wherein L" is as hereinbefore defined; preferably L" is hydrogen or a leaving group such as chloro.

In another aspect the present invention provides a compound of the formulae (IX):

(X)

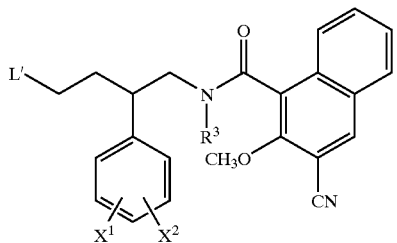

wherein R³, X¹, X² and L' are as hereinbefore defined.

It is well known in the art how to prepare optically-active forms (for example, by resolution of the racemic form or by synthesis from optically-active starting materials) and how to determine the $NK_1$ and $NK_2$ antagonist properties by the standard tests known in the art and those described hereinafter.

Some individual compounds within the scope of this invention may contain double bonds. Representations of double bonds in this invention are meant to include both the E and the Z isomer of the double bond. Additionally, some species within the scope of this invention may contain one or more asymmetric centers. This invention includes the use of any of the optically pure stereoisomers as well as any combination of stereoisomers.

The following biological test methods, data and Examples serve to illustrate and further describe the invention.

The utility of a compound of the invention or a pharmaceutically acceptable salt thereof (hereinafter, collectively referred to as a "compound") may be demonstrated by standard tests and clinical studies, including those disclosed in the publications described below.

SP Receptor Binding Assay (Test A)

The ability of a compound of the invention to antagonize the binding of SP at the $NK_1$ receptor may be demonstrated using an assay using the human $NK_1$ receptor expressed in Mouse Erythroleukemia (MEL) cells. The human $NK_1$ receptor was isolated and characterized as described in: B. Hopkins, et al. "Isolation and characterization of the human lung $NK_1$ receptor cDNA" *Biochem. Biophys. Res. Comm.*, 1991, 180, 1110–1117; and the $NK_1$ receptor was expressed in Mouse Erythroleukemia (MEL) cells using a procedure similar to that described in Test B below.

Neurokinin A (NKA) Receptor Binding Assay (Test B)

The ability of a compound of the invention to antagonize the binding of NKA at the $NK_2$ receptor may be demonstrated using an assay using the human $NK_2$ receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology*, 1994, 45, 9–19.

The selectivity of a compound for binding at the $NK_1$ and the $NK_2$ receptors may be shown by determining its binding at other receptors using standard assays, for example, one using a tritiated derivative of NKB in a tissue preparation selective for $NK_3$ receptors. In general, the compounds of the invention which were tested demonstrated statistically significant binding activity in Test A and Test B with a $K_i$ of 1 mM or much less typically being measured.

Rabbit Pulmonary Artery: $NK_1$ in vitro Functional Assay (Test C)

The ability of a compound of the invention to antagonize the action of the agonist Ac-[$Arg^6$, $Sar^9$, $Met(O_2)^{11}$] Substance P (6–11), ASMSP, in a pulmonary tissue may be demonstrated as follows.

Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs.

The segments are suspended between stainless steel stirrups, so as not to remove any of the endothelium, and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; indomethacin, 0.005 (to inhibit cyclooxygenase); and dl-Propranolol, 0.001 (to block β receptors); gassed continuously with 95% $O_2$—5% $CO_2$. Responses are measured on a Grass polygraph via Grass FT-03 transducers.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: $1 \times 10^{-6}$ M Thiorphan (to block E.C.3.4.24.11), $3 \times 10^{-8}$M (S)-N-[2-(3,4-dichlorophenyl)-4-[4-(2-oxoperhydropyrimidin-1-yl)piperidino]butyl]-N-methylbenzamide (to block $NK_2$ receptors), and the given concentration of the compound being tested. At the end of the 1.0 h equilibration, $3 \times 10^{-6}$M Phenylephrine hydrochloride is added for 1.0 h. At the end of 1.0 h, a dose relaxation curve to ASMSP is done. Each tissue is treated as a individual and is considered finished when it fails to relax further for 2 consecutive doses. When a tissue is complete, $1 \times 10^{-3}$M Papaverine is added for maximum relaxation.

Percent inhibition is determined when a tested compound produces a statistically significant (p<0.05) reduction of the total relaxation which is calculated using the total relaxation of the Papaverine as 100%. Potencies of the compounds are determined by calculating the apparent dissociation constants (KB) for each concentration tested using the standard equation:

$$KB=[\text{antagonist}]/(\text{dose ratio}-1)$$

where dose ratio=antilog[(agonist –log molar $EC_{50}$ without compound)–(–log molar $EC_{50}$ with compound)]. The $K_B$ values may be converted to the negative logarithms and expressed as –log molar KB (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as –log molar $EC_{50}$.

$NK_2$ in vitro Functional Assay (Rest D)

The ability of a compound of the invention to antagonize the action of the agonist [β-ala8] NKA (4–10), BANK, in a pulmonary tissue may be demonstrated as follows. Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and a small incision is made into the heart so that the left and right pulmonary arteries can be cannulated with polyethylene tubing (PE260 and PE190 respectively). The pulmonary arteries are isolated from the rest of the tissues, then rubbed over an intimal surface to remove the endothelium, and cut in half to serve as pairs. The segments are suspended between stainless steel stirrups and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; and indomethacin, 0.005 (to inhibit cyclooxygenase); gassed continuously with 95% $O_2$—5% $CO_2$. Responses are measured on a Grass polygraph via Grass FT-03 transducers.

Initial tension placed on each tissue is 2 g, which is maintained throughout the 45 min equilibration period. Tissues are washed with the physiological salt solution at 15 min intervals. After the 45 min equilibration period, $3 \times 10^{-2}$M KCl is given for 60 min to test the viability of the tissues. The tissues are then washed extensively for 30 min. The concentration of the compound being tested is then added for 30 min. At the end of the 30 min, a cumulative dose response curve to BANK is performed. Each tissue is treated as a individual and is considered finished when it fails to contract further for 2 consecutive doses. When a tissue is complete, $3 \times 10^{-2}$M $BaCl_2$ is added for maximum contraction.

Percent inhibition is determined when a tested compound produces a statistically significant (p<0.05) reduction of the total contraction which is calculated using the total contraction of the $BaCl_2$ as 100%. Potencies of the compounds are determined by calculating the apparent dissociation constants ($K_B$) for each concentration tested using the standard equation:

$$K_B=[\text{antagonist}]/(\text{dose ratio}-1)$$

where dose ratio=antilog[(agonist −log molar $EC_{50}$ without compound)−(−log molar $EC_{50}$ with compound)]. The $K_B$ values may be converted to the negative logarithms and expressed as −log molar $K_B$ (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as −log molar $EC_{50}$.

$NK_1$ and $NK_2$ in vivo Functional Assay (Test E)

The activity of a compound as an antagonist of $NK_1$ and/or $NK_2$ receptors also may be demonstrated in vivo in laboratory animals as described in: Buckner et al. "Differential Blockade by Tachykinin $NK_1$ and $NK_2$ Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." *J. Pharm. Exp. Ther.,* 1993, Vol 267(3), pp.1168–1175. The assay is carried out as follows.

Compounds are tested in anesthetized guinea pigs pretreated with i.v. indomethacin (10 mg/kg, 20 min), propranolol (0.5 mg/kg, 15 min), and thiorphan (10 mg/kg, 10 min).

Antagonists or vehicle are administered i.v. and orally, 30 and 120 min prior to increasing concentrations of agonist, respectively. The agonists used in these studies are ASMSP (Ac-[$Arg^6,Sar^9,Met(O_2)^{11}$]-SP(6–11)) and BANK (β-ala-8 NKA4–10).

Administered i.v., ASMSP is selective for $NK_1$ receptors, and BANK is selective for $NK_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm (−log$ED_{50}$). The $ED_{50}$ values, obtained in the presence (P) and absence (A) of antagonist, are used to calculate a Dose Ratio (P/A), an expression of potency. Data are expressed as mean±SEM and statistical differences were determined using ANOVA/Tukey-Kramer and Student's t-test, with $p<0.05$ considered statistically significant.

Compounds of the present invention exhibit marked activity in the foregoing tests and are considered useful for the treatment of those diseases in which the $NK_1$ and/or $NK_2$ receptor is implicated, for example, in the treatment of asthma and related conditions.

Clinical Studies

Clinical studies to demonstrate the efficacy of a compound of the invention may be carried out using standard methods. For example, the ability of a compound to prevent or treat the symptoms of asthma or asthma-like conditions may be demonstrated using a challenge of inhaled cold air or allergen and evaluation by standard pulmonary measurements such as, for example, FEV, (forced expiratory volume in one second) and FVC (forced vital capacity), analyzed by standard methods of statistical analysis.

It will be appreciated that the implications of a compound's activity in the above described Tests is not limited to asthma, but rather, that the Tests provide evidence of general antagonism of both SP and $NK_A$. SP and $NK_A$ have been implicated in the pathology of numerous diseases including: rheumatoid arthritis, Alzheimer's disease, cancer, schizophrenia, oedema, allergic rhinitis, inflammation, pain, gastrointestinal-hypermotility, anxiety, emesis, Huntington's disease, psychoses including depression, hypertension, migraine, bladder hypermotility and urticaria.

Accordingly, one feature of the invention is the use of a compound of formula I or a pharmaceutically acceptable salt thereof in the treatment of a disease in a human or other mammal in need thereof in which SP or $NK_A$ is implicated and antagonism of its action is desired.

Asthma is characterized by both chronic inflammation and hyperresponsiveness of the airways. The $NK_1$ receptor is known to mediate inflammation and mucus hypersecretion in airways; and the $NK_2$ receptor is involved in the control of the tone of bronchial smooth muscle. Thus, agents capable of antagonizing the actions of SP and NKA, at the $NK_1$ and $NK_2$ receptors, respectively, are capable of reducing both the chronic inflammation and the airway hyperresponsiveness which are symptomatic of asthma. It has been suggested that an antagonist having mixed affinity for $NK_1$ and $NK_2$ could be therapeutically superior to a receptor selective antagonist. C. M. Maggi "Tachykinin Receptors and Airway Pathophysiology" *EUR. Respir. J.,* 1993, 6, 735–742 at 739. Also, it has been suggested that a synergistic effect against bronchoconstriction may result from the simultaneous application of an $NK_1$ antagonist and an $NK_2$ antagonist. D. M. Foulon, et al. "$NK_1$ and $NK_2$ Receptors Mediated Tachykinin and Resiniferatoxin-induced Bronchospasm in Guinea Pigs" *American Review of Respiratory Disease,* 1993, 148, 915–921. Accordingly, another feature of the invention is the use of a compound of formula I or a pharmaceutically acceptable salt thereof in the treatment of asthma in a human or other mammal in need thereof. There is a possible role for Substance P antagonists in the treatment of depression. Accordingly, another feature of the invention is the use of a compound of formula (I) or a pharmaceutically acceptable salt thereof in the treatment of depression in a human or other mammal in need thereof.

Because of the range of effects attributable to the actions of SP and $NK_A$, compounds which are capable of blocking their actions may also be useful as tools for further evaluating the biological actions of other neurotransmitters in the tachykinin family. As a result, another feature of the invention is provided by the use of a compound of Formula I or a salt thereof as a pharmacological standard for the development and standardisation of new disease models or assays for use in developing new therapeutic agents for treating diseases in which SP or NKA are implicated or for assays for their diagnosis.

EXAMPLES

The invention will now be illustrated by the following non-limiting examples, in which, unless stated otherwise:

(i) temperatures are given in degrees Celsius (°C.); unless otherwise stated, operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 Pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition;

(vi) final products had satisfactory proton nuclear magnetic resonance (NMR) spectra;

(vii) when given, NMR data is in the form of delta values for major diagnostic protons, given in parts per million (ppm) relative to tetramethylsilane (TMS) as an internal standard, determined at 300 MHz using deuterated chloroform ($CDCl_3$) as solvent; conventional abbreviations for signal shape are used; for AB spectra the directly observed shifts are reported; coupling constants (J) are given in Hz; Ar designates an aromatic proton when such an assignment is made;

(viii) reduced pressures are given as absolute pressures in pascals (Pa); elevated pressures are given as gauge pressures in bars;

(ix) solvent ratios are given in volume:volume (v/v) terms; and (x) Mass spectra (MS) were run using an automated system with atmospheric pressure chemical ionization (APCI). Generally, only spectra where parent masses are observed are reported. The lowest mass major ion is reported for molecules where isotope splitting results in multiple mass spectral peaks (for example when chlorine is present).

Terms and abbreviations: Solvent mixture compositions are given as volume percentages or volume ratios. In cases where the NMR spectra are complex, only diagnostic signals are reported. atm; atmospheric pressure, Boc; t-butoxycarbonyl, Cbz; benzyloxycarbonyl, DCM; methylene chloride, DIPEA: diisopropylethylamine, DMF; N,N-dimethyl formamide, DMSO; dimethyl sulfoxide, $Et_2O$; diethyl ether, EtOAc; ethyl actate, h; hour(s), HPLC: high pressure liquid chromatography, min; minutes, NMR; nuclear magnetic resonance, psi; pounds per square inch, TFA; trifluoroacetic acid, THF; tetrahydrofuran.

Standard reductive amination refers to the typical procedure in which a solution of an amine (1–1.2 equivalents), an aldehyde (1–1.2 equivalents) and acetic acid (2 equivalents) are stirred in methanol for 5 to 60 min before adding $NaBH_3CN$ (1.7 equivalents). After 1–16 h the reaction is optionally concentrated, dissolved in DCM, and washed with saturated sodium bicarbonate and then purified by chromatography.

Standard Swern oxidation conditions refer to the oxidation of an alcohol to the corresponding aldehyde according to Mancuso, A J; Huang, S L; Swern, D; J. Org. Chem.; 1978,2840.

Standard formation of an acid chloride refers to the typical procedure in which a solution of a naphthoic or substituted naphthoic acid in DCM is stirred with 1–1.2 equivalents of oxalyl chloride and a catalytic amount of DMF for 1–12 h, concentrated under reduced pressure, and used without purification.

Standard acylation refers to the typical procedure in which an acid chloride (1–1.2 equivalents) is added to a stirred solution of an amine (1–1.2 equivalents) and triethylamine (2 equivalents) in DCM. After 1–16 h the reaction is optionally concentrated, dissolved in DCM, and washed with saturated sodium bicarbonate and then purified by chromatography.

Where noted that a final compound was converted to the citrate salt, the free base was combined with citric acid (1.0 equivalents) in methanol, concentrated under reduced pressure and dried under vacuum (25–70° C.). When indicated that a compound was isolated by filtration from $Et_2O$, the citrate salt of the compound was stirred in $Et_2O$ for 12–18 h, removed by filtration, washed with $Et_2O$, and dried under vacuum at 25–70° C.

Where noted that a final compound was converted to the hydrochloride salt, a solution of HCl in $Et_2O$ was added with stirring to a solution of the purified free base in DCM or methanol. The resulting precipitate was collected by filtration and dried under vacuum.

Each compound bearing a 2-substituted naphthamide existed as a mixture of conformational isomers (atropisomers); this is believed to result from slow rotation about the amide and/or aryl bonds. Such compounds showed multiple peaks in HPLC chromatograms and highly complex NMR spectra. In some cases, the individual components of an atropiomeric mixture could be purified by reverse phase HPLC and the properties could be independently evaluated.

Example 1

N-[(S)-2-(3,4-Dichlorophenyl)-4-[4-[tetrahydro-2-oxo-1(2H)-pyrimidinyl]-1-piperidinyl]-butyl]-N-methyl-2-methoxy-3-cyano-1-naphthamide citrate Using standard acylation conditions N-[(S)-2-(3,4-dichlorophenyl)-4-[4-[tetrahydro-2-oxo-1(2H)-pyrimidinyl]-1-piperidinyl]butyl]-N-methylamine (Miller, S C; WO 9505377) (0.130 g) was reacted with 2-methoxy-3-cyano-1-naphthoyl chloride (prepared from 3-cyano-1-naphthoic acid and oxalyl chloride) (0.065 g). The free base (0.110 g) was converted to the citrate salt. MS m/z 622 (M+H).

The requisite 2-methoxy-3-cyano-1-naphthoic acid was prepared as follows.

(a) 3-Hydroxy-4-iodo-2-naphthoic acid

A mixture of NaOH (2.12 g) in methanol (100 mL) was stirred until the solution was homogeneous. Sodium iodide (3.98 g) and 3-hydroxy-2-naphthoic acid (5.00 g) were added and allowed to stir for 30 min. The resulting suspension was cooled to 0° C. and a 5.25% (w/v) aqueous solution of sodium hypochlorite was added dropwise and stirring continued for 1 h. Saturated sodium thiosulfate (25 mL) was added and after 5 min the solution was acidified to pH 2 by addition of 6N HCl resulting in the formation of a yellow precipitate which was filtered and washed with water (50 mL). The precipitate was transferred to a round-bottomed flask, dissolved in methanol (70 mL) and toluene (100 mL), concentrated, redissolved in methanol (70 mL), concentrated, redissolved again in methanol (70 mL) and toluene (100 mL) and concentrated to afford the product as a yellow solid (6.26 g). MS m/z 313 (M−1). $^1$H NMR (DMSO-$d_6$): δ12.41 (broad, 1 H), 8.63 (s, 1 H), 8.05–7.97 (m, 2 H), 7.70 (m, 1 H), 7.42 (m, 1H).

(b) Methyl 3-methoxy-4-iodo-2-naphthoate

A solution of 3-hydroxy-4-iodo-2-naphthoic acid (8.0 g), dimethyl sulfate (8.03 g), powdered potassium carbonate (8.80 g), and dry acetone (150 mL) was heated under reflux for 18 h. The solution was cooled to room temperature, triethylamine (15 mL) was added, and stirring continued for 30 min. The solution was filtered through a pad of Celite and washed with dry acetone (50 mL). The filtrate was concentrated to a yellow oil, diluted with EtOAc, and washed successively with 1N HCl (100 mL), saturated aqueous sodium bicarbonate (100 mL), and brine (100 mL). The organic phase was dried (sodium sulfate), filtered, concentrated, and purified by chromatography (0–10% EtOAc in hexanes) to afford the product as a yellow oil (5.53 g). $^1$H NMR (DMSO-$d_6$) δ8.47 (s, 1 H), 8.09 (m, 2 H), 7.74 (m, 1 H), 7.61 (m, 1 H), 3.94 (s, 3 H), 3.87 (s, 3 H).

(c) 1-Iodo-2-methoxy-3-cyanonaphthalene

Based on the procedure of Wood, J L; Khatri, N A; Weinreb, S M; Tetrahedron Lett; 51, 4907 (1979), methyl 3-methoxy-4-iodo-2-naphthoate (5.0 g) was suspended in xylenes (100 mL), cooled to 0° C., dimethylaluminum amide solution (approximately 37 mmol) was added and the solution heated under reflux for 2.5 h. The solution was then cooled to 0° C. and the solution was acidified to pH 2 by addition of 1N HCl and extracted with EtOAc (3×100 mL).

The combined EtOAc extracts were washed with saturated aqueous sodium bicarbonate (150 mL) and brine (150 mL), dried (sodium sulfate), filtered, concentrated, and purified by chromatography (1:1 EtOAc:DCM, then 10–20% EtOAc in DCM) to afford the product as a white solid (3.29 g). $^1$H NMR (DMSO-$d_6$): δ8.69 (s, 1 H), 8.24–8.04 (m, 2 H), 7.91–7.81 (m, 1 H), 7.76–7.65 (m, 1 H), 3.99 (s, 3 H); MS m/z 311 (M+H).

(d) Methyl 2-methoxy-3-cyano-1-naphthoate

Through a suspension of 1-iodo-2-methoxy-3-cyanonaphthalene (0.250 g), Pd(OAc)$_2$ (0.018 g), triethylamine (0.081 g) and methanol (20 mL) was bubbled carbon monoxide for 25 min, then stirred at 70° C. under carbon monoxide (1 atm) for 18 h. The cooled solution was filtered, rinsed with methanol (20 mL) and DCM (20 mL), concentrated, preadsorbed onto silica (1 g) and purified by chromatography (0–10% EtOAc in hexanes) to afford the product as a white solid (0.113 g). $^1$H NMR (DMSO-$d_6$): δ8.78 (s, 1 H), 8.12–8.09 (m, 1 H), 7.84–7.78 (m, 2 H), 7.70–7.63 (m, 1 H), 4.02–4.01 (m, 6 H); IR (cm$^{-1}$): 2228, 1724, 1296, 1236, 1208, 1017.

(e) 2-Methoxy-3-cyano-1-naphthoic acid

A solution of methyl 2-methoxy-3-cyano-1-naphthoate (0.113 g) and LiOH.H$_2$O (0.0196 g) THF (3 mL), water (1 mL) and methanol (1 mL) was stirred overnight at room temperature. The solution was diluted with saturated sodium bicarbonate and extracted with Et$_2$O. The aqueous layer was acidified to pH 2 by addition of 1N HCl and extracted with Et$_2$O. The organic layer was washed with water (30 mL) and brine (40 mL), dried (sodium sulfate), filtered, and concentrated to a white solid. $^1$H NMR (DMSO-$d_6$): δ14.06 (broad, 1 H), 8.08–8.02 (m, 1 H), 7.83–7.76 (m, 2 H), 7.69–7.63 (m, 1 H), 4.02 (s, 3 H); MS m/z: 226 (M−1).

Example 2

N-[(S)-2-(3,4-Dichlorophenyl)-4-{4-(2-oxo-1-piperidinyl)-4-(N-methylaminocarbonyl)}-1-piperidinyl]butyl]-N-methyl-3-cyano-2-methoxy-1-naphthamide 4-(2-Oxo-1-piperidinyl)-4-(methylaminocarbonyl)piperidine (Miller, S C; Jacobs, R T; Shenvi, A B; EP 739891) was reacted with N-[2-(S)-(3,4-dichlorophenyl)-4-oxobutyl]-N-methyl-3-cyano-2-methoxy-1-naphthamide according to standard reductive amination methodology to give the title compound which was converted to the citrate salt according to the standard procedure. $^1$H NMR (300 MHz, DMSO-$d_6$) δ8.70–8.63 (m), 8.08–7.91 (m), 7.77–7.72 (m), 7.68 (s), 7.66–7.61 (m), 7.58–7.54 (m), 7.49–7.47 (m), 7.39–7.33 (m), 7.06 (s), 7.03 (s), 6.88–6.79 (m), 6.30–6.28 (d), 4.55–4.47 (t), 4.12–3.99 (m), 3.92 (s), 3.88 (s), 3.82–3.77 (m), 3.69 (s), 3.50–3.39 (m), 3.17–3.13 (m), 3.06–2.81 (m), 2.72–2.57 (m), 2.22–2.01 (m), 1.79 (bs), 1.66–1.64 (m), 1.11–0.853 (m); MS APCI, m/z=678 (M$^+$); Analysis calculated for $C_{36}H_{41}N_5O_4Cl_2$, 1 citric acid, 1.34 water, C, 56.36; H, 5.82; N, 7.82; found C, 56.34; H, 5.73; N, 7.80.

The requisite N-[2-(S)-(3,4-dichlorophenyl)-4-oxobutyl]-N-methyl-3-cyano-2-methoxy-1-naphthamide was prepared as follows:

(a) N-[2-(S)-(3,4-Dichlorophenyl)-4-hydroxybutyl]-N-methyl-3-cyano-2-methoxy-1-naphthamide N-[(S)-2-(3,4-Dichlorophenyl)-4-hydroxybutyl]-N-methylamine (Miller, S C; WO 9512577) dissolved in DCM and added to a 10% aqueous sodium bicarbonate solution. The mixture was cooled to 0° C. and a solution of 3-cyano-2-methoxy-1-naphthoyl chloride in DCM was added dropwise over 30 min. After stirring overnight the organic phase was concentrated, and purified by column chromatography to afford N-[2-(S)-(3,4-dichlorophenyl)-4-hydroxybutyl]-N-methyl-3-cyano-2-methoxy-1-naphthamide [$^1$H NMR (300 MHz, DMSO-$d_6$) δ9.70–9.64 (m), 8.67–8.57 (m), 8.07–7.97 (m), 7.80 (s), 7.72–7.55 (m), 7.52–7.48 (m), 7.40–7.33 (m), 7.12–7.10 (d), 7.04–7.02 (d), 6.87–6.83 (m), 6.37–6.29 (d), 4.53–4.44 (t), 4.11–4.00 (m), 3.94 (s), 3.92 (s), 3.91–3.73 (m), 3.71 (s), 3.45–3.38 (m), 3.33 (s), 3.14 (s), 2.97–2.95 (d), 2.63 (s), 2.60 (s); MS APCI, m/z=455 (M$^+$)].

(b) N-[2-(S)-(3,4-Dichlorophenyl)-4-oxobutyl]-N-methyl-3-cyano-2-methoxy-1-naphthamide The alcohol from (a) was oxidized using oxalyl chloride and DMSO under standard Swern conditions to afford the aldehyde [$^1$H NMR (300 MHz, DMSO-$d_6$) δ9.70–9.64 (m), 8.67–8.57 (m), 8.07–7.97 (m), 7.80 (s), 7.72–7.55 (m), 7.52–7.48 (m), 7.40–7.33 (m), 7.12–7.10 (d), 7.04–7.02 (d), 6.87–6.83 (m), 6.37–6.29 (d), 4.53–4.44 (t), 4.11–4.00 (m), 3.94 (s), 3.92 (s), 3.91–3.73 (m), 3.71 (s), 3.45–3.38 (m), 3.33 (s), 3.14 (s), 2.97–2.95 (d), 2.63 (s), 2.60 (s); MS APCI, m/z=455 (M$^+$)].

Example 3

N-[(S)-2-(3,4-Dichlorophenyl)-4-[4-(2-oxo-1-piperidinyl)-4-(N-methylaminocarbonyl)]-1-piperidinyl]butyl]-3-cyano2-methoxy-1-naphthamide citrate 3-Cyano-2-ethyl4-methoxy-1-naphthoic acid (60 mg) was added to anhydrous DCM (15 mL) and DIPEA (0.11 mL) was added and the mixture stirred under nitrogen until the carboxylic acid was dissolved. Then tetramethyl fluoroformamidinium hexafluorophosphate (TFFH) (76 mg) was added in a single portion. After 20 min, a solution of N-[(S)-2-(3,4-dichlorophenyl)-4-[4-(2-oxo-1-piperidinyl)-4-(N-methylaminocarbonyl)]-1-piperidinyl]-butyl]-amine, (120 mg) DCM was added. After 1 h, water was added and the layers separated. The product was recovered as a white powder (100 mg, 57%) after extraction and chromatographic purification (10–20% methanol in DCM), and converted to the citrate salt under standard conditions. $^1$H NMR (300 MHz, DMSO-$d_6$) δ8.72 (m), 8.62 (s), 8.01 (d), 7.67–7.50 (m), 7.39–7.36 (m), 7.14 (d), 4.11–4.09 (m), 3.88 (s), 3.78–3.59 (m), 3.39–3.04 (m), 2.67–2.50 (m), 2.20–2.08 (m), 1.94–1.8 (m), 1.79–1.64 (m), 1.26–1.24 (d); MS APCI, m/z=664.36 (M$^+$).

The requisite N-[(S)-2-(3,4-dichlorophenyl)-4-[4-(2-oxo-1-piperidinyl)-4-(N-methylaminocarbonyl)]-1-piperidinyl]butyl]-amine was prepared as follows.

(a) N-[(S)-2-(3,4-Dichlorophenyl)-4-[4-(2-oxo-1-piperidinyl)-4-(N-methylaminocarbonyl)]-1-piperidinyl]butyl]-phthalimide N-[(S)-2-(3,4-dichlorophenyl)-4-oxobutyl]-phthalimide (Bernst 709376, 1996) was reacted with 4-(2-oxo-1- piperidinyl)-4-(N-methylaminocarbonyl)piperidine using standard reductive amination conditions to afford the product as a white powder (200 mg, 52%) after extraction and chromatographic purification (5–10% methanol in DCM). 1H NMR (300 MHz, DMSO-d6) d 7.81 (s), 7.53 (s), 7.47–7.42 (d), 7.20–7.14 (m), 3.86–3.72 (m), 3.49–3.27 (m), 3.21–3.14 (m), 2.55–2.47 (m), 2.44–2.27 (m), 2.18–2.14 (t), 2.08–1.99 (m), 1.95–1.84 (m), 1.74–1.59 (m); MS APCI, m/z=584.18 (M−).

(b) N-[(S)-2-(3,4-Dichlorophenyl)-4-[4-(2-oxo-1-piperidinyl)-4-(N-methylaminocarbonyl)]-1-piperidinyl]butyl]-amine This compound was synthesized from N-[(S)-2-(3,4-dichlorophenyl)-4-oxobutyl]-phthalimide according to the method in step 4 for Example to afford the amine as a white powder (120 mg, 91%) after filtering concentrating the mother liquor followed by ether trituration. $^1$H NMR (300 MHz, DMSO-d$_6$) δ7.54–7.51 (d), 7.45 (s), 7.21–7.14 (m), 3.41–3.29 (m), 2.89–2.67 (m), 2.63–2.60 (m), 2.50–2.40 (m), 2.38–2.26 (m), 2.18–2.14 (t), 2.05–1.86 (m), 1.76–1.72 (m), 1.66–1.56 (m); MS APCI, m/z=453.54 (M−).

Example 4

N-[2-(S)-(3,4-Dichlorophenyl)-4-[4-(2-oxo-1-piperidinyl)-4-N,N-dimethylaminocarbonyl)]-1-piperidinyl]butyl]-N-methyl-3-cyano-2-methoxy-1-naphthamide citrate Using standard reductive amination conditions, N-[2-(S)-(3,4-dichlorophenyl)]-4-oxobutyl-N-methyl-3-cyano-2-methoxy-1-naphthamide (0.200 g) was reacted with 4-(2-oxo-1-piperidinyl)-4-(N,N-dimethylaminocarbonyl) piperidine (0.122 g) and converted to the citrate salt. $^1$H NMR (300 MHz, DMSO-d$_6$) δ8.70–8.63 (m), 8.08–6.82 (m), 6.32–6.29 (m), 4.55–4.51 (m), 4.125–3.69 (m), 3.38–1.61 (m); MS APCI, m/z=714 (M+Na).

Example 5

N-[2-(S)-(3,4-Dichlorophenyl)-4-[4-(tetrahydro-2-oxo-1(2H)-pyrimidinyl)-4-(methylaminocarbonyl)]-1-piperidinyl]butyl]-N-methyl-3-cyano-2-methoxy-1-naphthamide citrate Using standard reductive amination conditions, N-[2-(S)-(3,4-dichlorophenyl)]-4-oxobutyl-N-methyl-3-cyano-2-methoxy-1-naphthamide (0.200 g) was reacted with N-methyl-4-(tetrahydro-2-oxo-1(2H)-pyrimidinyl)-piperidine-4-carboxamide (Miller, S C. WO 9512577) (0.116 g) and converted to the citrate salt. $^1$H NMR (300 MHz, DMSO-d$_6$) δ8.70–8.63 (m), 8.08–6.78 (m), 6.35–6.30 (m), 4.54–4.46 (m), 4.11–1.87 (m); MS APCI, m/z=701 (M+N Example 6

N-[2-(S)-(3,4-Dichlorophenyl)-4-[4-(S,S-dioxo-tetrahydro-2H-1,2-thiazin-2-yl)-4-(methylaminocarbonyl)-1-piperidinyl]butyl]-N-methyl-3-cyano-2-methoxy-1-naphthamide citrate 4-(S,S-Dioxo-tetrahydro-2H-1,2-thiazin-2-yl)-4-(methylaminocarbonyl)]-1-piperidine trifluoroacetate was neutralized with triethylamine, then reacted with N-[2-(S)-(3,4-dichlorophenyl)]-4-oxobutyl-N-methyl-2-methoxy-3-cyano-1-naphthamide and triethylamine under standard reductive amination conditions to afford the product (50% over two steps) and converted to the citrate salt. $^1$H NMR (300 MHz, DMSO-d$_6$) δ8.64 (d), 8.11–7.30 (m), 7.05–6.77 (m), 6.32 (d), 4.50 (m), 4.10–3.93 (m), 3.93 (d), 3.93–1.20 (m). MS APCI, m/z=(M); 714.

The requisite 4-(S,S-dioxo-tetrahydro-2H-1,2-thiazin-2-yl)-4-(methylaminocarbonyl)]-1-piperidine was prepared as follows.

(a) 4-Bromobutane-1-sulfonyl chloride

4-Bromo-1-butane sulfonic acid sodium salt (1.25 g) was added to thionyl chloride (12.5 mL) with stirring under nitrogen. The reaction was heated under reflux for 3 h, cooled, and concentrated under reduced pressure. The residue was then diluted with diethyl ether, washed with water, dried, filtered and concentrated under reduced pressure to afford 760 mg of a 7:3 mixture of desired product and the 4-chloro analog (instead of the 4-bromo). $^1$H NMR (300 MHz, CDCl$_3$) δ3.70 (t, 2H), 3.46 (t, 2H), 2.25 (m, 2H), 2.09 (m, 2H).

(b) 1-N-Cbz-[4-(4-Amino-4-methylaminocarbonyl)]-1-piperidine

1-N-Cbz-4-Amino-4-piperidylcarboxylic acid (3.0 g) was suspended in THF (100 mL) under nitrogen. To this was added, at 50° C. with stirring, as a solution in THF, triphosgene (1.3 g), over 5 min. The reaction was stirred 0.5 h at 50° C., then allowed to cool to room temperature. It was then concentrated under reduced pressure and the residue dissolved in 100 mL THF. A solution of methylamine (8.1 mL, 2.0M in THF) was added at 5° C. and the reaction allowed to stir overnight. It was then diluted with EtOAc, washed with water, then brine, dried, filtered and concentrated under reduced pressure. The resulting oil was then passed through a plug of silica (5% MeOH in DCM) to afford 1.65 g of the desired product as a white solid. 1H NMR (300 MHz, CDCl3) d 7.63 (bs, 1H), 7.35 (m, 5H), 5.13 (s, 2H), 4.05 (d, 2H), 3.15 (t, 2H), 2.80 (d, 3H), 2.18 (m, 2H), 1.37 (m, 4H); MS APCI, m/z=(M+); 2.92.

(c) 1-N-Cbz-[4-[4-Bromobutylsulfonamido-4-methylaminocarbonyl]]-1-piperidine

To a stirred solution of 940 mg of 1-N-Cbz-[4-(4-Amino-4-methylaminocarbonyl)]-1-piperidine and 750 mg of a 7:3 mixture of 4-bromo-1-butanesulfonyl chloride and 4-chloro-1-butanesulfonyl chloride in 20 mL of DCM at 0° C. under nitrogen was slowly added 0.49 mL of triethylamine. The reaction was stirred overnight at room temperature, then additional triethylamine (0.49 mL) was added. The mixture was stirred for 3 days, concentrated under reduced pressure, and purified by chromatography (3–4% MeOH in DCM) to afford 380 mg of the desired product as a mixture of alkyl bromide and alkyl chloride adducts. $^1$H NMR (300 MHz, CDCl$_3$) δ7.36 (m, 5H), 6.22 (m, 1H), 5.13 (s, 2H), 4.69 (s, 1H), 3.84 (m, 2H), 3.57 (t, 2H), 3.45 (m, 4H), 3.06 (t, 2H), 2.87–2.79 (m, 3H), 2.01 (m, 8H). MS APCI, m/z=(M+); 446.

(d) 4-[(S,S-Dioxo-tetrahydro-2H-1,2-thiazin-2-yl)-4-(methylaminocarbonyl)]-1-N-Cbz-1-piperidine To a stirred solution of 380 mg of 1-N-Cbz-[4-[4-bromobutylsulfonamido-4-methylaminocarbonyl]]-1-piperidine (containing the alkyl chloride impurity from the prior step) in 5 mL THF under nitrogen was added 40 mg of sodium hydride (60% dispersion in mineral oil) and the reaction was heated under reflux for 6 h. Additional sodium hydride (20 mg, 60% dispersion) was added and the reaction heated under reflux overnight. It was then cooled; diluted with EtOAc; washed with water, then brine; dried, filtered and concentrated under reduced pressure. The residue was purified by chromatography (3% MeOH in DCM) to afford 110 mg of the desired product as an oil. $^1$H NMR (300 MHz, CDCl$_3$) δ7.35 (m, 5H), 6.57 (m, 1H), 5.07 (s, 2H), 3.71 (m, 2H), 3.56 (m, 2H), 3.40 (m, 2H), 3.09 (m, 2H), 2.85 (d, 3H), 2.20 (m, 6H), 1.73 (m, 2H). MS APCI, m/z=(M$^+$); 410.

(e) 4-[(S,S-Dioxo-tetrahydro-2H-1,2-thiazin-2-yl)-4-(methylaminocarbonyl)]-piperidine trifluoroacetate 4-[(S,S-Dioxo-tetrahydro-2H-1,2-thiazin-2-yl)-4-(methylaminocarbonyl)]-1-N-Cbz-1-piperidine (110 mg) was dissolved in 10 mL of TFA under nitrogen and heated under reflux for 40 min. The reaction was cooled and concentrated under reduced pressure, dissolved in DCM, and concentrated again to afford the desired product which was used directly in the subsequent reaction. $^1$H NMR (300 MHz, CDCl$_3$) δ6.60 (m, 1H), 3.46 (t, 2H), 3.21 (t, 4H), 3.12 (t, 2H), 2.85 (d, 3H), 2.40 (m, 4H), 2.20 (m, 2H), 1.75 (m, 2H), 0.88 (m, 1H). MS APCI, m/z=(M$^+$); 276.

Example 7

N-[2-(S)-(3,4-Dichlorophenyl)-4-[4-(methylsulfonyl-(N-methyl)amino)-4-(methylaminocarbonyl)]-1-piperidinyl]butyl]-N-methyl-3-cyano-2-methoxy-1-naphthamide citrate 4-[4-(Methylsulfonyl-(N-methyl)amino)-4-(methylaminocarbonyl)]-piperidine trifluoroacetate was reacted with N-[2-(S)-(3,4-dichlorophenyl)]-4-oxobutyl-N-methyl-2-methoxy-3-cyano-1-naphthamide under standard reductive amination conditions in the presence of triethylamine to afford the product (90% over two steps) and converted to the citrate salt. $^1$H NMR (300 MHz, DMSO-d$_6$) δ8.64 (d), 8.01 (m), 7.79–7.48 (m), 7.37 (m), 7.04 (d), 6.83 (m), 6.30 (d), 4.52 (t), 4.06–3.93 (m), 3.93 (d), 3.93–2.97 (m); 2.97(d); 2.97–2.00(m); MS APCI, m/z=(M$^+$); 688.

(a) 4-[4-(Methylsulfonylamino)-4-(methylaminocarbonyl)]-1-N-Cbz-piperidine

To a solution of 500 mg of 4-[4-amino-4-(methylaminocarbonyl)]-1-N-Cbz-piperidine in 10 mL DCM at 5° C. under nitrogen was added 0.15 mL of methanesulfonyl chloride, then 0.29 mL of triethylamine. The reaction was stirred at room temperature for 2 h, diluted with DCM, washed successively with 0.5 N aqueous HCl, water, brine then dried and filtered. The solution was concentrated under reduced pressure to afford 500 mg of the desired compound as a foam solid. $^1$H NMR (300 MHz, CDCl$_3$) δ7.35 (m, 5H), 6.41 (m, 1H), 5.57 (s, 1H), 5.13 (s, 2H), 3.92 (d, 2H), 3.29 (t, 2H), 3.00 (s, 3H), 2.86 (d, 3H), 2.04 (m, 4H); MS APCI, m/z=(M$^+$); 370.

(b) 4-[4-(Methylsulfonyl-(N-methyl)amino)-4-(methylaminocarbonyl)]-1-N-Cbz-piperidine To a solution of 80 mg of 4-[4-(methylsulfonylamino)-4-(methylaminocarbonyl)]-1-N-Cbz-piperidine in 10 mL THF/DMF (1:1) under nitrogen was added 32 mg potassium t-butoxide, then 0.015 mL iodomethane. The reaction was allowed to stir at room temperature for 3 h. It was then diluted with EtOAc, washed with water, then brine, dried, filtered and concentrated under reduced pressure. The residue was purified via reverse phase HPLC to afford 4-[4-(methylsulfonyl-(N-methyl)amino)-4-(methylaminocarbonyl)]-1-N-Cbz-piperidine as an oil (50% yield). $^1$H NMR (300 MHz, CDCl$_3$) δ7.35 (m, 5H), 6.32 (bs, 1H), 5.13 (s, 2H), 3.93 (d, 2H), 3.40 (bs, 2H), 2.92 (s, 3H), 2.91 (s, 3H), 2.84 (d, 3H), 2.30 (d, 2H), 2.00 (bs, 2H); MS (APCI, negative ion mode) m/z=(M$^-$); 382. This material was N-Cbz deprotected according to the methods described for Example 6, step (e) to afford 4-[4-(Methylsulfonyl-(N-methyl)amino)-4-(methylaminocarbonyl)]-piperidine trifluoro-acetate.

Example 8

N-[2-(S)-(3,4Dichlorophenyl)-4-(3-morpholinon-4-yl)-4-methylaminocarbonyl-1-piperidinyl]butyl]-N-methyl-3-cyano-2-methoxy-1-naphthamide citrate 4-(3-Morpholinone-4-yl)-4-methylaminocarbonyl-piperidine was reacted with N-[2-(S)-(3,4-dichlorophenyl)]-4-oxobutyl-N-methyl-3-cyano-2-methoxy-1-naphthamide using standard reductive amination conditions to afford the product (43% over two steps) and converted to the citrate salt. $^1$H NMR (300 MHz, DMSO-d$_6$) δ8.65 (d), 8.03 (m), 7.78–7.31 (m), 7.07–6.79 (m), 6.32 (d), 4.52 (t), 4.17–4.01 (m), 4.00 (d), 3.94 (d), 3.93–3.70 (m), 3.50–1.97 (m). MS APCI, m/z=(M$^+$); 680.

The requisite 4-(3-morpholinon-4-yl)-4-methylaminocarbonyl-piperidine was prepared as follows.

(a) 4-Bromomethylcarbonylamino-4-methylaminocarbonyl-1-N-Cbz-1-piperidine

4-Amino-4-methylaminocarbonyl-1-N-Cbz-1-piperidine (700 mg) was dissolved in THF (15 mL) under nitrogen and cooled to −10° C. Bromoacetyl bromide (0.22 mL), then triethylamine (0.38 mL) were slowly added. The cooling bath was removed and the reaction allowed to stir for 1 h. It was then diluted with EtOAc; washed with water and brine; dried, filtered and concentrated under reduced pressure. The residue was purified by chromatography (2–3% MeOH in DCM) to afford the desired product (740 mg) as a foam solid. $^1$H NMR (300 MHz, CDCl$_3$) δ7.35 (m, 5H), 6.83 (bs, 1H), 6.46 (s, 1H), 5.13 (s, 2H), 3.90 (m, 4H), 3.21 (m, 2H), 2.81 (d, 3H), 2.13 (m, 4H). MS APCI, m/z=(M+Na); 434.

(b) 4-Chloroethoxymethylcarbonylamino-4-methylaminocarbonyl-1-N-Cbz-1-piperidine To a stirred solution of 730 mg of 4-bromomethylcarbonylamino4-methylaminocarbonyl-1-N-Cbz-1-piperidine in 10 mL of THF under nitrogen was added 0.32 mL of 2-chloroethanol. The reaction was then cooled to −10° C. and 90 mg of 60% sodium hydride was added. It was then allowed to warm to room temperature over 1 h. after which a small amount of water was added. The reaction was then diluted with EtOAc; washed with water, then brine; dried, filtered and concentrated under reduced pressure. The residue was purified by chromatography to afford 580 mg of the desired compound as a gum. $^1$H NMR (300 MHz, CDCl$_3$) δ7.35 (m, 5H), 7.10 (m, 1H), 6.80 (s, 1H), 5.13 (s, 2H), 4.03 (s, 2H), 3.85 (m, 4H), 3.70 (t, 2H), 3.24 (m, 2H), 2.80 (d, 3H), 2.15 (m, 4H). MS APCI, m/z=(M$^+$); 412.

(c) 4-(3-Morpholinon-4-yl)-4-methylaminocarbonyl-1-N-Cbz-1-piperidine

To a solution of 4-chloroethoxymethylcarbonylamino-4-methylaminocarbonyl-1-N-Cbz-1-piperidine (580 mg) in THF under nitrogen was added sodium hydride (70 mg, 60% dispersion in mineral oil). The reaction was heated under reflux for 2 h and additional 30 mg sodium hydride (60%) was added. The mixture was heated under reflux for additional 2 h, cooled, and quenched with water. The reaction was then diluted with EtOAc; washed with water, brine; dried, filtered and concentrated under reduced pressure. The residue was purified via chromatography (3–5% MeOH in DCM) to afford the desired product (300 mg) as a foam solid. $^1$H NMR (300 MHz, CDCl$_3$) δ7.35 (m, 5H), 6.77 (m, 1H), 5.13 (s, 2H), 4.16 (s, 2H), 3.80 (t, 2H), 3.66 (m, 2H), 3.49 (m, 2H), 3.41 (t, 2H), 2.81 (d, 3H), 2.40 (m, 2H), 2.16 (m, 2H). MS APCI, m/z=(M$^-$); 374.

(d) 4-(3-Morpholinone-4-yl)-4-methylaminocarbonyl-piperidine 4-(3-Morpholinone-4-yl)-4-methylaminocarbonyl-1-N-Cbz-1-piperidine (300 mg) was dissolved in 2-propanol (20 mL) under nitrogen and to this was added 10% palladium on carbon (170 mg). The mixture was then placed under 50 psi. of hydrogen, with shaking, for 1.5 h. It was then filtered and concentrated under reduced pressure to afford the desired compound which was used directly in the subsequent reaction. $^1$H NMR (300 MHz, CDCl$_3$) δ6.78 (m, 1H), 4.16 (s, 2H), 3.84 (t, 2H), 3.46 (t, 2H), 2.94 (m, 4H), 2.82 (d, 3H), 2.40 (m, 2H), 2.21 (m, 2H). MS APCI, m/z=(M$^+$); 242.

Example 9

N-[2-(S)-(3,4Dichlorophenyl)-4-[4-(methylsulfonylamino)-4-(methylaminocarbonyl)]-1-piperidinyl]butyl]-N-methyl-3-cyano-2-methoxy-1-naphthamide citrate N-(4-[4-(Methylsulfonylamino)-4-(methylaminocarbonyl)piperidine (Example 7) was reacted with N-[2-(S)-(3,4-dichlorophenyl)]-4-oxobutyl-N-methyl-3-cyano-2-methoxy-1-naphthamide under standard reductive amination conditions to afford the product (70% over two steps) and converted to the citrate salt. $^1$H NMR (300 MHz, DMSO-d$_6$) d 8.64 (d), 8.04 (m), 7.22–7.79 (m), 7.04 (d), 6.88 (d), 6.79 (d), 6.33 (d), 4.50 (t), 3.95–4.09 (m), 3.95–4.09 (m), 3.94 (d),, 3.64–3.92 (m), 2.90–3.51 (m), 2.89 (d), 2.46–2.87 (m), 2.04 (m); MS APCI, m/z=(M+); 674. The requisite N-(4-[4-(methylsulfonylamino)-4-(methylaminocarbonyl)piperidine was prepared by treatment of N-(4-[4-(methylsulfonylamino)-4-(methylaminocarbonyl)-N-1-Cbz-piperidine (Example 7, step (a)) with TFA according to the procedure of Example 6, step (e) and the resulting trifluoroacetate salt was neutralized by addition of triethylamine.

Example 10

N-[(S)-2-(3,4-Dichlorophenyl)-4-[4-(2-oxo-1-piperidinyl)-4-(pyrrolidin-1-yl-carbonyl)]-1-piperidinyl]butyl]-3-cyano-2-methoxy-1-naphthamide citrate Using standard reductive amination conditions N-[2-(S)-(3,4-dichlorophenyl)]-4-oxobutyl-N-methyl-3-cyano-2-methoxy-1-naphthamide (0.287 g) was reacted with 4-[4-(2-oxo-1-piperidinyl)-4-(pyrrolidin-1-yl-carbonyl)]-1-piperidine (Miller, S C; WO 9512577) (0.181g). The resulting reaction mixture was purified by chromatography and the title compound was isolated as a citrate salt. MS m/z 718 (M+); $^1$H NMR (DMSO d$_6$) δ8.6 (m, 1H), 8.0 (m, 1H), 7.8–7.3 (m, 5H), 7.1–6.3 (m, 1H), 4.5 (t, J=10 Hz, 1H), 3.95 (s, 3H), 2.2 (m, 3H), 2.0–1.6 (m, 8H); mp 168–175 (d).

Example 11

N-[(S)-2-(3,4-Dichlorophenyl)-4-[4-(2-oxo-1-piperidinyl)-4-(hydroxyethylaminocarbonyl)]-1-piperidinyl]butyl]-3-cyano-2-methoxy-1-naphthamide citrate Using standard reductive amination conditions N-[2-(S)-(3,4-dichlorophenyl)]-4-oxobutyl-N-methyl-3-cyano-2-methoxy-1-naphthamide (0.173 g) was reacted with 4-[4-(2-oxo-1-piperidinyl)-4-(hydroxyethylaminocarbonyl)]-piperidine (0.181 g). The resulting reaction mixture was purified by chromatography to afford the desired product. MS m/z 708 (M+); $^1$H NMR (DMSO d$_6$) δ8.6 (m, 1H), 8.0(m, 1H), 7.8–7.3 (m, 5H), 7.1–6.3 (m, 1H), 4.5 (t, J=10 Hz, 1H), 4.4 (t, J=5 Hz, 1H), 3.95 (s, 3H), 2.2 (m, 3H), 2.0–1.6 (m, 8H); mp 110–120 (d).

The requisite 4-[4-(2-oxo-1-piperidinyl)-4-(hydroxyethylaminocarbonyl)]-piperidine was prepared as follows.

(a) 4-[4-(2-Oxo-1-piperidinyl)-4-(hydroxyethylaminocarbonyl)]-1-N-Cbz-piperidine A solution of 4-[4-(2-oxo-1-piperidinyl)-4-carboxy]-1-N-Cbz-piperidine (Miller, S C; WO 9512577) (2.88 g) in DCM (20 mL) was treated with diisopropylethylamine (3.05 mL) and tetramethylfluoroformamidinum hexafluorophosphate (2.64 g) and stirred for 2 h. To this was added a solution of 2-aminoethanol (0.128 g) in 5 mL of DCM containing diisopropylethylamine (0.364 g) and the reaction mixture was stirred for 2 h. At the end of this period the reaction mixture was diluted with EtOAc, washed with 5% hydrochloric acid and saturated sodium bicarbonate, dried, concentrated under reduced pressure, and purified by chromatography to afford the product (0.475 g). MS (APCI, negative ion mode) m/z 402 (M–); $^1$H NMR (CDCl$_3$) δ7.4 (m, 5H), 6.6 (t, J=5 Hz, 1H), 5.1 (m, 2H), 3.8–3.2 (m, 10H), 2.4 (t, J=10 Hz, 2H), 2.3–1.6 (m, 11H).

(b) 4-[4-(2-oxo-1-piperidinyl)-4-(hydroxyethylaminocarbonyl)]-piperidine

A solution of 4-[4-(2-oxo-1-piperidinyl)-4-(hydroxyethylaminocarbonyl)]-1-N-Cbz-piperidine (0.36 g) in ethanol (50 mL) containing acetic acid (0.1 mL) and 10% Pd/C (50 mg) was hydrogenated over an atmosphere of hydrogen at 40 psi for 16 h. The mixture was filtered and concentrated under reduced pressure to afford the product (0.268 g): MS m/z 270 (M+); $^1$H NMR (CDCl$_3$) δ6.9 (m, 1H), 3.6 (m, 1H), 3.4–3.1(m, 8H), 2.4–2.2 (m, 3H), 2.0–1.6 (m, 8H).

Example 12

N-[(S)-2-(3,4-Dichlorophenyl)-4-[4-(2-oxo-1-piperidinyl)-4-(aminocarbonylmethylaminocarbonyl)]-1-piperidinyl]butyl]-3-cyano-2-methoxy-1-naphthamide citrate Using standard reductive amination conditions N-[2-(S)-(3,4-dichlorophenyl)]-4-oxobutyl-N-methyl-3-cyano-2-methoxy-1-naphthamide (0.227 g) was reacted with 4-[4-(2-oxo-1-piperidinyl)-4-(aminocarbonylmethylaminocarbonyl)]-piperidine (0.375 g) (prepared according to the method described for Example 11 except glycinamide was used in place of aminoethanol). The resulting reaction mixture was purified by chromatography to afford the desired product: MS m/z 721 (M+); $^1$H NMR (DMSO d$_6$) δ8.6 (m, 1H), 8.0(m, 1H), 7.8–3(m, 9H), 4.5(t, J=10 Hz, 1H), 4.4 (t, J=5 Hz, 1H), 3.95(s, 3H), 2.2 (m, 3H), 2.0–1.6 (m, 8H); mp 140–145 (d).

Example 13

N-[(S)-2-(3,4-Dichlorophenyl)-4-[4-(2-oxo-1-piperidinyl)-4(cyanomethylaminocarbonyl)]-1-piperidinyl]butyl]-3-cyano-2-methoxy-1-naphthamide citrate Using standard reductive amination conditions N-[2-(S)-(3,4-dichlorophenyl)]-4-oxobutyl-N-methyl-3-cyano-2- methoxy-1-naphthamide (0.316 g) was reacted was reacted with 4-[4-(2-oxo-1-piperidinyl)-4-(cyanomethylaminocarbonyl)]-piperidine (0.375 g) (prepared according to the method described for Example 11 except aminoacetonitrile was used in place of aminoethanol). The resulting reaction mixture was purified by chromatography to afford the desired product. MS m/z 703 (M+); $^1$H NMR (DMSO d$_6$) δ8.6 (m, 1H), 8.0(m, 1H), 7.8–6.3(m, 6H), 4.5 (t, J=10 Hz, 1H), 4.4 (t, J=5 Hz, 1H), 3.95(s, 3H), 3.3 (m, 4H), 2.2 (m, 3H), 2.0–1.6 (m, 8H); mp 130–145 (d).

$C_{1-6}$alkylcarbamoyl, di-$C_{1-6}$alkylcarbamoyl, $C_{1-6}$alkanoyl, $C_{1-6}$alkanoylamino, and aminosulfonyl;

$R^5$ is independently selected from hydroxy, cyano, nitro, trifluoromethoxy, trifluoromethyl, $C_{1-6}$alkylsulfonyl, halo, $C_{1-6}$alkoxy, $C_{1-6}$alkyl, cyano$C_{1-6}$alkyl, $C_{2-6}$alkenyl, $C_{2-6}$alkynyl, carboxy, $C_{1-6}$alkoxycarbonyl, carbamoyl, $C_{1-6}$alkylcarbamoyl, di-$C_{1-6}$alkylcarbamoyl, $C_{1-6}$alkanoyl, $C_{1-6}$alkanoylamino, aminosulfonyl, and $C_{1-6}$alkyl substituted with a group selected from hydroxy, cyano, nitro, carboxy, trifluoromethoxy, trifluoromethyl, halo,

TABLE 1

Selected experimental data for Tachykinin antagonists. 2-Dichlorophenyl-butyl chiral center is of the (S) configuration. These materials were prepared by reductive amination using procedures and intermediates as described within the above text or elsewhere. Compounds containing a base nitrogen were converted to citrate salts.

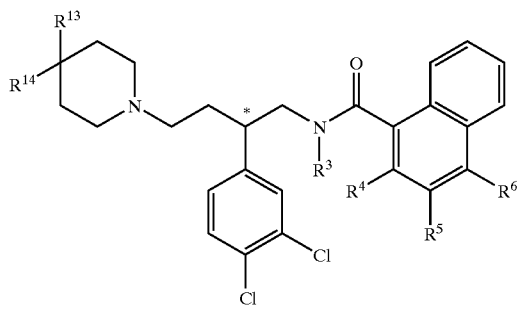

| | $R^3$ | $R^4$ | $R^5$ | $R^6$ | $R^{13}$ | $R^{14}$ | MS (m/z) |
|---|---|---|---|---|---|---|---|
| 14* | —Me | —OCH$_2$O— | | —H | —(2-oxopiperidin-1-yl) | —C(O)NHMe | 667 |
| 15 | —Et | —OMe | —CN | —H | —(2-oxopiperidin-1-yl) | —C(O)NHCH$_2$CH$_2$OH | 722 |
| 16 | —Et | —OMe | —CN | —H | —(2-oxopiperidin-1-yl) | —C(O)NHCH$_2$C(O)NH$_2$ | 735 |
| 17 | —Et | —OMe | —CN | —H | —(2-oxopiperidin-1-yl) | —C(O)NHCH$_2$CN | 717 |
| 18 | —Et | —OMe | —CN | —H | —(tetrahydro-2-oxo-1(2H)-pyrimidin-1-yl) | —C(O)NHMe | 693 |
| 19 | —Et | —OMe | —CN | —H | —(2-oxopiperidin-1-yl) | —C(O)NHMe | 692 |
| 20 | —Et | —OMe | —CN | —H | —(2-oxopiperidin-1-yl) | H | 635 |
| 21 | —Et | —OMe | —CN | —H | —(tetrahydro-2-oxo-1(2H)-pyrimidin-1-yl) | H | 636 |

*Naphtho[2,3-d]-1,3-dioxole-4-carboxylic acid was prepared according to Dallacker, F.; et al.; Z. Naturforsch; 1979, 1434.

What is claimed is:

1. A compound having the formula

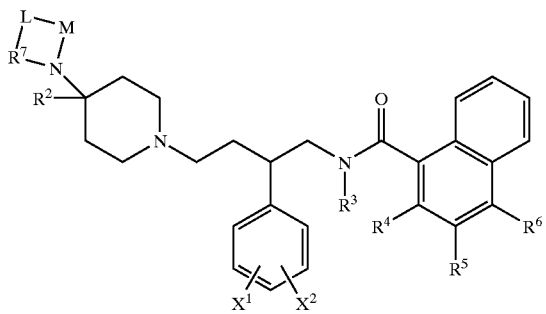

wherein:

$R^2$ is hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl or di-$C_{1-6}$alkylcarbamoyl;

$R^3$ is H or $C_{1-6}$alkyl;

$R^4$ is independently selected from hydroxy, halo, $C_{1-6}$alkoxy, $C_{1-6}$alkyl, cyano$C_{1-6}$alkyl, $C_{2-6}$alkenyl, $C_{2-6}$alkynyl, carboxy, $C_{1-6}$alkoxycarbonyl, carbamoyl, $C_{1-6}$alkylcarbamoyl, di-$C_{1-6}$alkylcarbamoyl, $C_{1-6}$alkanoyl, $C_{1-6}$alkanoylamino, and aminosulfonyl;

$C_{1-6}$alkylsulfonyl, $C_{1-6}$alkoxy, $C_{1-6}$alkyl, cyano$C_{1-6}$alkyl, $C_{2-6}$alkenyl, $C_{2-6}$alkynyl, $C_{1-6}$alkoxy-carbonyl, $C_{1-6}$alkylcarbamoyl, di__$C_{1-6}$alkylcarbamoyl, $C_{1-6}$alkanoyl or $C_{1-6}$alkanoylamino; or $R^4$ and $R^5$ together form —OCH$_2$O— or —OC(CH$_3$)$_2$O—;

$R^6$ is selected from hydrogen, hydroxy, cyano, nitro, trifluoromethoxy, trifluoromethyl, $C_{1-6}$alkylsulfonyl, halo, $C_{1-6}$alkoxy, $C_{1-6}$alkyl, cyano$C_{1-6}$alkyl, $C_{2-6}$alkenyl, $C_{2-6}$alkynyl, carboxy, $C_{1-6}$alkoxycarbonyl, carbamoyl, $C_{1-6}$alkylcarbamoyl, di-$C_{1-6}$alkylcarbamoyl, $C_{1-6}$alkanoyl, $C_{1-6}$alkanoylamino, aminosulfonyl, and $C_{1-6}$alkyl substituted with a group selected from hydroxy, cyano, nitro, carboxy, trifluoromethoxy, trifluoromethyl, halo, $C_{1-6}$alkylsulfonyl, $C_{1-6}$alkoxy, $C_{1-6}$alkyl, cyano$C_{1-6}$alkyl, $C_{2-6}$alkenyl, $C_{2-6}$alkynyl, $C_{1-6}$alkoxy-carbonyl, $C_{1-6}$alkylcarbamoyl, di-$C_{1-6}$alkylcarbamoyl, $C_{1-6}$alkanoyl or $C_{1-6}$alkanoylamino;

$R^7$ is —CH$_2$CH$_2$—, —CH$_2$CH$_2$CH$_2$— or —CH$_2$CH$_2$CH$_2$CH$_2$—;

M is —C(=O)— or —S(=O)$_2$—;

L is —NH— or —CH$_2$—; and $X^1$ and $X^2$ are independently H or halogen, wherein at least one of $X^1$ and $X^2$ are halogen; and a pharmaceutically-acceptable salt thereof.

2. A compound according to claim 1 wherein:
$R^7$ is —CH$_2$CH$_2$CH$_2$—.

3. A compound according to claim 2 wherein:
$R^2$ is hydrogen, hydroxy, methoxycarbonyl, methylcarbamoyl or dimethylcarbamoyl.

4. A compound according to claim 3 wherein:
M is —C(=O)—; and
L is —CH$_2$—.

5. A compound according to claim 2, wherein:
$R^3$ is hydrogen, methyl or ethyl;
$R^4$ is $C_{1-4}$alkoxy, $C_{1-4}$alkyl, halogen, —CH=CHCH$_3$, —S(O)$_n$CH$_3$, or —OS(O)$_2$CH$_3$;
$R^5$ is cyano, nitro, hydrogen or halogen;
$R^6$ is hydrogen, methoxy, cyano or nitro; and
n is 0, 1 or 2.

6. A compound according to claim 3, wherein:
$R^3$ is hydrogen, methyl or ethyl;
$R^4$ is $C_{1-4}$alkoxy, $C_{1-4}$alkyl, halogen, —CH=CHCH$_3$, —S(O)$_n$CH$_3$, or —OS(O)$_2$CH$_3$;
$R^5$ is cyano, nitro, hydrogen or halogen;
$R^6$ is hydrogen, methoxy, cyano or nitro; and
n is 0, 1 or 2.

7. A compound according to claim 4, wherein:
$R^3$ is hydrogen, methyl or ethyl;
$R^4$ is $C_{1-4}$alkoxy, $C_{1-4}$alkyl, halogen, —CH=CHCH$_3$, —S(O)$_n$CH$_3$, or —OS(O)$_2$CH$_3$;
$R^5$ is cyano, nitro, hydrogen or halogen;
$R^6$ is hydrogen, methoxy, cyano or nitro; and
n is 0, 1 or 2.

8. A compound according to claim 5, wherein:
$R^3$ is hydrogen, methyl or ethyl;
$R^4$ is methyl, ethyl, methoxy, ethoxy, hydroxy or fluoro;
$R^5$ is cyano or nitro; and
$R^6$ is hydrogen.

9. A compound according to claim 6, wherein:
$R^3$ is hydrogen, methyl or ethyl;
$R^4$ is methyl, ethyl, methoxy, ethoxy, hydroxy or fluoro;
$R^5$ is cyano or nitro; and
$R^6$ is hydrogen.

10. A compound according to claim 7, wherein:
$R^3$ is hydrogen, methyl or ethyl;
$R^4$ is methyl, ethyl, methoxy, ethoxy, hydroxy or fluoro;
$R^5$ is cyano or nitro; and
$R^6$ is hydrogen.

11. A process for preparing a compound according to any one of claims 1–4, in which process comprises the step of:
reacting a compound of the formula (III) with a compound of the formula (IV) under reductive amination conditions:

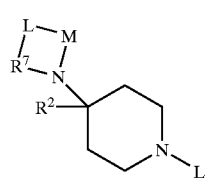
(III)

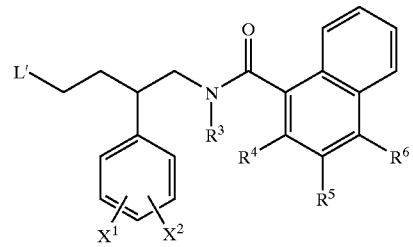
(IV)

wherein L, M, $R^2$ through $R^7$, $X^1$ and $X^2$ are as in claim 1; and L and L' are groups such that reductive amination of the compounds of the formulae (III) and (IV) forms a N—C bond; or reacting a compound of the formula (V) with a compound of the formula (VI):

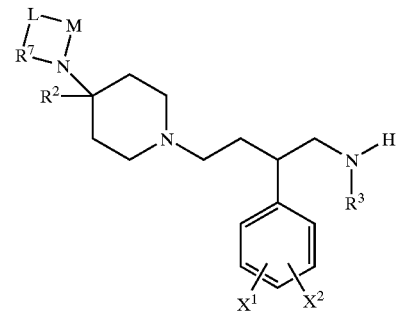
(V)

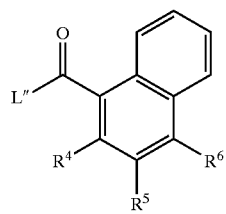
(VI)

wherein L, M, $R^2$ through $R^7$, $X^1$ and $X^2$ are as defined in claim 1; and L" is a leaving group.

12. A pharmaceutical composition comprising a compound according to any one of claims 1–4 or 5–10, and a pharmaceutically-acceptable diluent or carrier.

13. A method of treating depression, anxiety, asthma, rheumatoid arthritis, schizophrenia, oedema, allergic rhinitis, pain, gastrointestinal-hypermotility, emesis, Huntington's disease, psychoses, hypertension, migraine, bladder hypermotility, or urticaria comprising administering an effective amount of a compound according to any one of claims 1–4 or 5–10.

* * * * *